United States Patent [19]
Koritz

[11] 4,102,656
[45] Jul. 25, 1978

[54] ODOR CONDITIONER

[76] Inventor: Bjorn R. Koritz, 1641 Third Ave., New York, N.Y. 10028

[21] Appl. No.: 726,721

[22] Filed: Sep. 27, 1976

[30] Foreign Application Priority Data

Sep. 25, 1975 [CH] Switzerland .................... 107516/75

[51] Int. Cl.² ............................................ B01D 46/00
[52] U.S. Cl. ...................................... 55/210; 55/234; 55/417; 55/418; 55/473; 55/481; 55/504; 261/99; 261/107; 21/74 R
[58] Field of Search ................ 55/210, 212, 234, 417, 55/418, 467, 504, 470–473, 481, 511; 21/74 R; 261/99, 107

[56] References Cited

U.S. PATENT DOCUMENTS

| 1,451,329 | 4/1923 | Dressler | 261/99 |
| 1,916,907 | 7/1933 | Sargent | 261/99 |
| 3,168,917 | 2/1965 | Bartels | 55/DIG. 31 |
| 3,278,175 | 10/1966 | Hirtz | 261/99 |
| 3,861,894 | 1/1975 | Marsh | 261/99 |
| 3,950,155 | 4/1976 | Komiyama | 55/210 |
| 3,951,625 | 4/1976 | Follette | 55/481 |

Primary Examiner—Bernard Nozick
Attorney, Agent, or Firm—Blum, Moscovitz, Friedman & Kaplan

[57] ABSTRACT

An apparatus supplies to a selected region air laden with a vapor which may be a scent or a masking odor. The device may be controlled to hold the level of vapor in the selected region at a desired value. Provision is made for prevention of the loss of the compound to be volatilized when the device is not in use as well as when in use.

10 Claims, 5 Drawing Figures

ODOR CONDITIONER

BACKGROUND OF THE INVENTION

A number of circumstances may make it desirable to introduce selected compounds in vapor form into the air which we breathe. One of such circumstances is the desire to associate a pleasnt odor with a commerical establishment. A second circumstance is a desire to induce a prospective customer to purchase a specific perfume. A third circumstance is to mask an unpleasant odor. The perception of an unpleasant odor may also be masked by introducing into the air compounds which deaden odor-sensing receptors in the olfactory system.

With regard to treating the air when unpleasant aromas are present, it has previously been the practice to attempt to remove the unpleasant aroma. This is an expensive proposition, particularly, for instance, at the entrance to a store. Consequently, the overcoming of unpleasant aromas by the introduction of more pleasant aromas has been the more general practice. Conventionally, in such cases, pleasant aromas are introduced in aerosol form. However, aerosol droplets are relatively large, as compared to individual molecules, so that this method of dispensing the desired material is relatively expensive. A less expensive, but equally effective means, is therefore to be desired.

A further problem which arises in connection with dispensing of odors is control over the dosage. Where there are strong draughts present, or in relatively open spaces, the quantity to be dispensed is, of necessity, larger. Therefore, provision for controlling the rate of introduction of the essence or aromatic material into the air is desirable. Such control is afforded by the present invention.

SUMMARY OF THE INVENTION

A housing includes a slot into which a conditioning element may be inserted, the conditioning element containing a reservoir for a volatile compound to be dispensed and a filter element which is permeable to air and which is readily wetted by the compound in the reservoir, the filter element dipping into the reservoir.

The housing includes a fan or blower for forcing air through the filter element, the selected compound evaporating from the surface of the filter element into the air stream. The housing can be connected to tubing or ducting for leading the vapor-laden airstream to a region distant from the apparatus.

The housing has walls at the inlet and outlet ends thereof, each wall including an opening and a cover for the opening which can be closed when the apparatus is not in use. The openings can be covered either manually or automatically.

In a preferred arrangement, the size of at least one of the openings or, alternatively, the speed of the fan can be adjusted to control the airflow rate and thus the rate at which the aroma is introduced into the selected region. A sensor which is sensitive to the concentration of the selected compound can be connected to automatic controller means for holding the concentration of the compound in the ambient air at the selected region at a selected value. Control of the airflow rate can also be carried out by way of a sensor which is sensitive to air motion in the selected region.

Accordingly, an object of the present invention is an apparatus for conditioning air in a selected region with respect to aroma.

Another object of the present invention is an apparatus for introducing a selected aroma at a selected level into a selected region.

A further object of the present invention is an apparatus for introducing a selected aroma or masking odor or compounds for deadening olfactory nerves into a selected region of ambient air.

Yet another object of the present invention is an apparatus for controlling the odor in a selected region, the apparatus including automatic means for protection against loss of valuable compounds when the apparatus is not in use and for controlling the rate of flow of air therethrough in response to ambient air conditions.

Still other objects and advantages of the invention will in part be obvious and will in part be apparent from the specification.

The invention accordingly comprises the features of construction, combination of elements, and arrangement of parts which will be exemplified in the construction hereinafter set forth and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
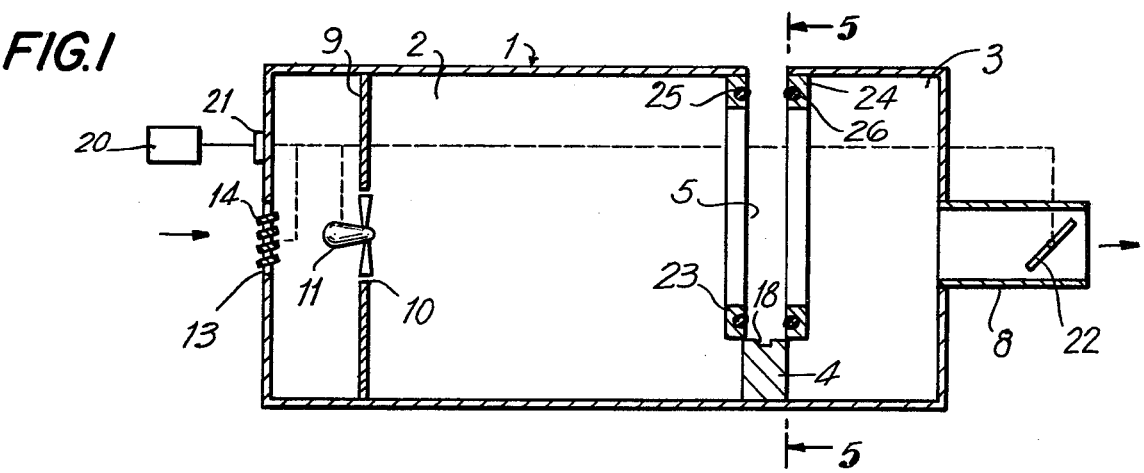
FIG. 1 is a side elevational view of the housing portion of the apparatus of the present invention.
Figure 2:
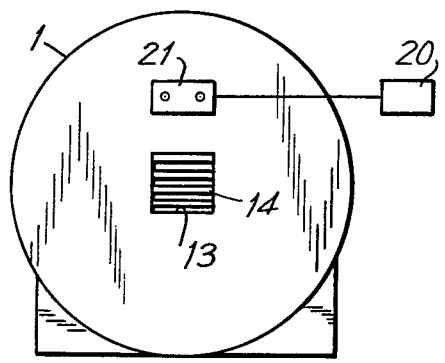
FIG. 2 is a left end view of said housing portion.

Apparatus in accordance with the present invention includes a housing indicated in FIG. 1 generally by the reference numeral 1 divided by a gap or slot 5 into an inlet end 2 and an outlet end 3. The left end of the housing 1 is closed by an end wall 31 having an opening 13 therein through which air may be introduced. A cover 14 for opening 13 is provided, the cover as shown in FIG. 1 being in the form of louvres. The right-hand end of housing 1 is closed by a wall 32 also having an opening therein, the opening in the embodiment shown being in the form of a tube 8 for connection to exterior ducting or tubing (not shown). In the embodiment shown, means for controlling the rate of airflow through the apparatus in the form of a damper 22 is shown.

Airflow through the apparatus is provided by means of a fan or blower 11. The fan 11 may be supported directly from the housing 1 as by struts (not shown) or may be fitted into opening 10 in partition 9 as shown in FIG. 1.

A conditioning element 19 fits within slot 5. Conveniently, a base 4 is provided in the bottom portion of gap 5 to act as a support for the conditioning element 19. Conveniently, base 4 may have a groove 18 therein to aid in positioning conditioning element 19 by coacting with tongue 18a at the bottom of conditioning element 19.

Figure 3:
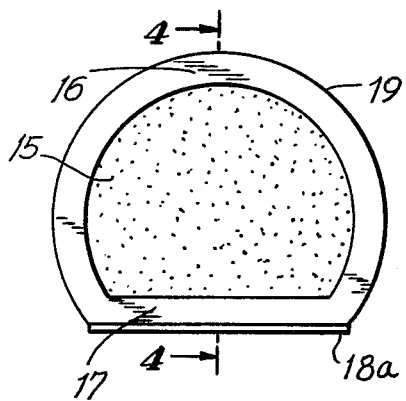
FIG. 3 is a front view of a conditioning element for use in combination with said housing.

Conditioning element 19 has a reservoir portion 17 at the bottom thereof for holding a volatile fluid to be vaporized therefrom. A filter element 15 is held in frame 16 of conditioning element 19 so that filter element 15 dips into reservoir 17 and any liquid therein. The filter element is made of an air permeable material which is wet essentially uniformly with the liquid in reservoir 17, as by capillarity. In the form shown in FIG. 3, conditioning element 15 is in essentially sheet form, but as is evident, may be constructed in cylindrical or other forms as are conventionally known. It is only necessary that the filter element 15 be so disposed that air moved by fan or blower 11 must traverse same when the apparatus is in operation.

Figure 4:
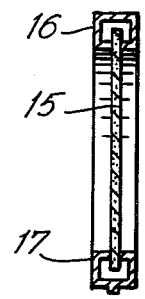
FIG. 4 is a view along line 4-4 of FIG. 3.
Figure 5:
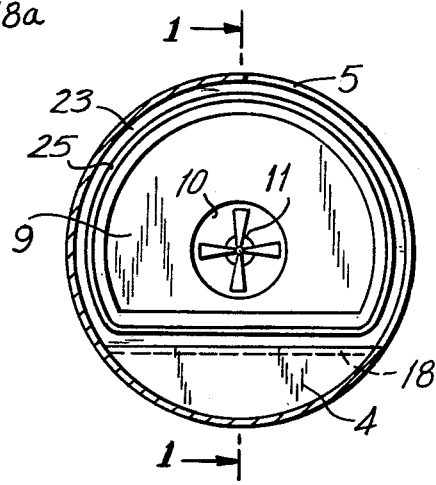
FIG. 5 is a view along line 5-5 of FIG. 1.

The manner in which filter element 15 is held in frame 16 so that it dips into reservoir 17 and completely covers the exposed region of frame 16 is shown in FIG. 4.

As aforenoted, it is desirable that it be possible to control the airflow rate through said apparatus. This can be effected by controlling the positioning of cover 14 in opening 13 or damper 22 in tube 8. The same objective can be effected by controlling the speed of fan or blower 11. For such purpose, fan 11 may be of the conventional 3-speed type or electronic means of control may be employed.

For automatic control of the airflow rate through said apparatus, a sensor positioned in the region which is to be aroma-conditioned is operatively connected to a controller means 21. Sensor means 20 may detect the actual level of the selected compound used for odor-conditioning of the air in the selected region or may sense air motion which removes the odor-control ingredient from the selected region. Controller 21, in response to the signal from sensor 20, then controls the flow rate of air through the apparatus by controlling the positioning of cover 14 or damper 22 or by controlling the rate of rotation of fan 11. As is obvious, a variable-pitch fan or blower could be used, control of airflow rate then being achieved by varying the pitch of the blades.

In view of the fact that the aroma-producing compound in reservoir 17 may be valuable, it is desirable to prevent losses thereof either during operation or when the system is shut down. So far as preventing losses is concerned, cover 14 and damper 22 can be closed either manually or automatically by controller means 21. When the apparatus is in operation, loss can occur principally by leakage in the join between conditioning element 19 and housing 1. To prevent such loss, flanges 23 and 24 containing O-rings 25 and 26 are provided in housing 1 around the periphery of slot 5. Flange 16 in conditioning element 19 engages said O-rings sealingly so that loss of the aroma constituent from the apparatus during operation is negligible.

Filter element 15 may be of a fabric, either woven or non-woven. As aforenoted, said fabric must be air-permeable. Further, it must wet uniformly. Depending on the choice of volatile compound to be vaporized, said fabric may be of cellulose, polyester, nylon or other synthetic fiber.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language might be said to fall therebetween.

I claim:

1. Apparatus for odor conditioning of ambient air by the introduction of a vapor of a selected liquid into a selected region or space, comprising a housing defining a chamber having an inlet end and an outlet end, a partition in said chamber, said partition having an opening therein, a first wall terminating said chamber at said inlet end, a second wall terminating said chamber at said outlet end, an electric fan for moving air from said inlet end to said outlet end, said fan being mounted in said opening in said partition, said housing having a slot therein dividing said chamber and separating said inlet from said outlet end, and a conditioning element for insertion fittingly in said slot, said conditioning element including a reservoir for said selected liquid, a frame having an opening therethrough and a wicking air-permeable filter element covering said opening, said frame holding said filter element and said reservoir so that said filter element dips into said reservoir and covers the slot between said inlet and outlet ends so that air moving from said inlet end to said outlet end of said chamber must pass through said filter element for accepting vapor of said selected liquid, said filter element holding said liquid by reason of its wicking characteristic, said first wall having therein a first opening for admitting air and first cover means for closing said first opening, and said second wall having therein a second opening for efflux of air containing the vapor of said selected liquid from said outlet end and second cover means for closing said second opening.

2. The apparatus as defined in claim 1, wherein said housing and said conditioning element are constructed for engaging each other sealingly, to minimize loss of said selected liquid at said slot.

3. The apparatus as defined in claim 1, further comprising connecting means for connecting said second opening in said second wall with exterior ducting for leading said vapor to said selected region when said selected region is at a distance from said apparatus.

4. The apparatus as defined in claim 1, wherein said filter element is a fabric in sheet form.

5. The apparatus as defined in claim 4, wherein said fabric is capillarily active with reference to said selected liquid.

6. The apparatus as defined in claim 1, further comprising controller means for closing said first and second openings by means of said first and second cover means when said apparatus is out of use for conservation of said selected compound.

7. The apparatus as defined in claim 6, further comprising sensor means for determining the concentration of vapor of said liquid in said selected region, said sensor means being connected with said controller means, and airflow-rate adjustment means under the control of said controller means for holding the concentration of said vapor at a selected level in said selected region.

8. The apparatus as defined in claim 7, wherein said airflow-rate adjustment means is said fan, said fan being constructed for selectively controlling the rate at which air is moved thereby through said housing.

9. The apparatus as defined in claim 7, wherein said airflow-rate adjustment means is said first cover means, said first cover means being constructed for controlling the size of said first opening.

10. The apparatus as defined in claim 9, wherein said airflow-rate adjustment means is said second cover means, said second cover means being constructed for controlling the size of said second opening.

* * * * *

UNITED STATES PATENT OFFICE
CERTIFICATE OF CORRECTION

PATENT NO. : 4,102,656
DATED : July 25, 1978
INVENTOR(S) : Bjorn R. Koritz

It is certified that error appears in the above–identified patent and that said Letters Patent are hereby corrected as shown below:

On the title page, in INID Code 30:

Cancel "Switzerland" and substitute --Sweden--.

Signed and Sealed this

Eleventh Day of September 1979

[SEAL]

Attest:

LUTRELLE F. PARKER
*Attesting Officer*   *Acting Commissioner of Patents and Trademarks*